US004001737B2

United States Statutory Invention Registration [19]

[11] Reg. Number: H1737

[45] Published: Jun. 2, 1998

Swaminathan et al.

[54] 7-OXABICYCLOHEPTANE CARBOXYLIC ACID PROSTAGLANDIN ANALOG INTERMEDIATES USEFUL IN THE PREPARATION OF ANTI-THROMBOTIC AND ANTI-VASOSPASTIC COMPOUNDS AND METHOD FOR PREPARING SAME

[75] Inventors: Shankar Swaminathan, North Brunswick; Philip M. Sher, Plainsboro; Ambarish Singh, Bordentown; Wen-Sen Li, Holmdel; John J. Venit, North Brunswick, all of N.J.

[73] Assignee: Bristol-Myers Squibb Company, Princeton, N.J.

[21] Appl. No.: 828,460

[22] Filed: Mar. 28, 1997

[51] Int. Cl.[6] ..... C07D 263/52

[52] U.S. Cl. ..... 548/217

*Primary Examiner*—Charles T. Jordan
*Assistant Examiner*—Meena Chelliah
*Attorney, Agent, or Firm*—Burton Rodney

[57] ABSTRACT

A method is provided for preparing intermediates for 7-oxabicycloheptane carboxylic acid intermediates of the structures -continued wherein R is alkyl, aryl, arylalkyl or cycloalkyl;

$R^1$ is alkyl, arylalkyl or cycloalkyl; $R^2$ is aryl or arylalkyl; and of the structure where R and $R^1$ are as defined above, which may be used in making the final anti-thrombotic—anti-vasospastic compounds.

22 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

7-OXABICYCLOHEPTANE CARBOXYLIC ACID PROSTAGLANDIN ANALOG INTERMEDIATES USEFUL IN THE PREPARATION OF ANTI-THROMBOTIC AND ANTI-VASOSPASTIC COMPOUNDS AND METHOD FOR PREPARING SAME

FIELD OF THE INVENTION

The present invention relates to novel 7-oxabicycloheptane carboxylic acid prostaglandin analog intermediates which may be used to prepare a final anti-thrombotic—anti-vasospastic product, and to methods for preparing same.

BACKGROUND OF THE INVENTION

U.S. Pat. No. 5,100,889 to Misra et al discloses 7-oxabicycloheptyl substituted heterocyclic amide prostaglandin analogs which are thromboxane $A_2$ ($TXA_2$) receptor antagonists or combined thromboxane $A_2$ receptor antagonist/thromboxane synthetase inhibitors useful, for example, in the treatment of thrombotic and/or vasospastic diseases, and have good duration of action. Examples of compounds disclosed in Misra et al have the structural formula I

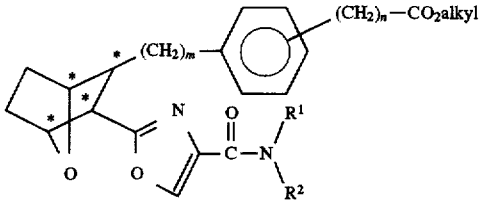

I and including all stereoisomers thereof, wherein m is 1, 2 or 3; n is 0, 1, 2, 3 or 4;

$R^1$ is hydrogen, lower alkyl, aralkyl, aryl, cycloalkyl, cycloalkylalkyl, or amide

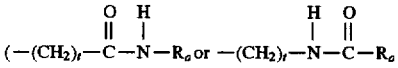

wherein t is 1 to 12 and $R_a$ is lower alkyl, aryl, cycloalkyl, or cycloalkylalkyl);

$R^2$ is hydrogen, lower alkyl, aryl, or aralkyl; or $R^1$ and $R^2$ together with the nitrogen to which they are linked may form a 5- to 8- membered ring.

Misra et al disclose that these compounds may be prepared by transmetallating bromophenylalkyl B

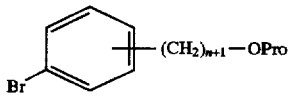

by treatment with t-$C_4H_9$Li or n-C4H9Li or subjecting B to a Grignard reaction by treatment with Mg, and then condensing with the perhydro benzopyran-3-ol derivative or the perhydro benzofuran-1-ol derivative C

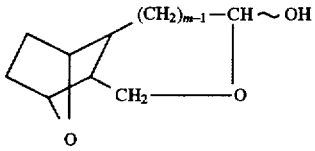

C to form the condensed 7-oxabicycloheptane alcohol compound of the structure Z

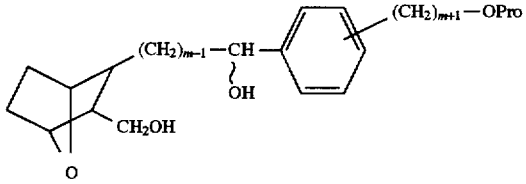

Z and then subjecting the condensed compound to hydrogenolysis to form the following alcohol

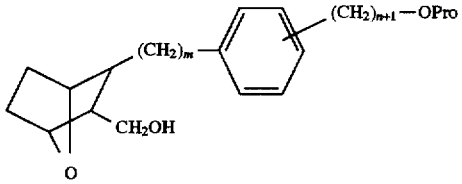

D

Where Pro is thexyldimethylsilyl or t-butyldimethylsilyl, the alcohol is acetylated and the silyl protecting group of the so-formed acetate is removed to form the following acetate:

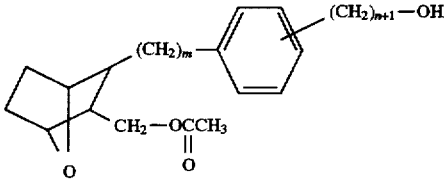

which is treated with a protecting compound and the acetate is removed by treatment with aqueous hydroxide or excess methyllithium to form the following alcohol:

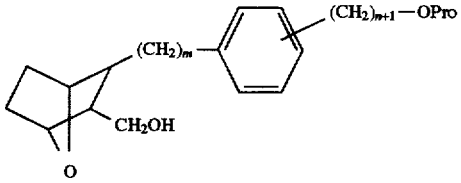

D'

(where Pro is t-butyldiphenylsilyl). The protected alcohol is subjected to a Jones oxidation to form the following acid:

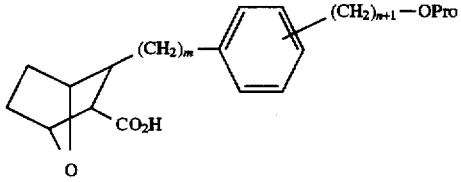

The so-formed carboxylic acid intermediate is then employed to make the final compound.

In a more preferred procedure, Misra et al disclose protecting the alcohol function of alcohol Z to form the protected alcohol

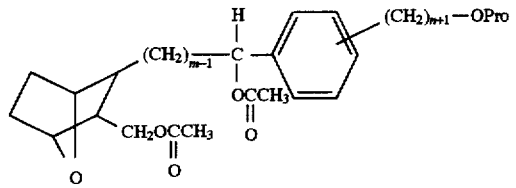

subjecting the protected alcohol to a Jones oxidation and esterification to form the ester

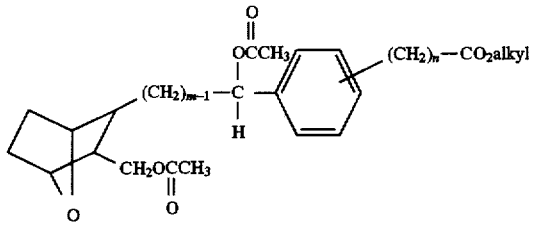

which is made to undergo hydrogenolysis and subsequent removal of the acetate protecting group by transesterification to afford the alcohol

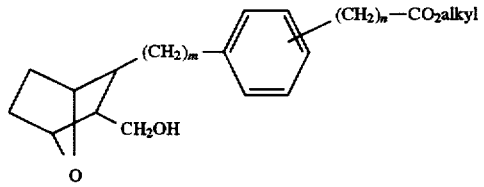

which is subjected to a Jones oxidation to form the carboxylic acid intermediate II

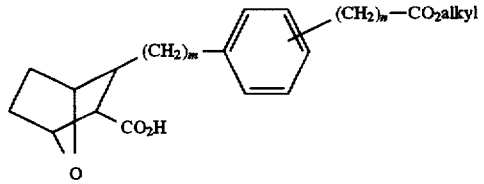

In an alternative procedure where n is 1, the above carboxylic acid intermediate II is formed by treating D' with acetic anhydride and removing the protecting group to form the acetate alcohol

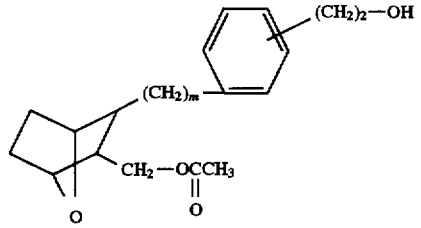

which is made to undergo a Dess-Martin oxidation to form the aldehyde

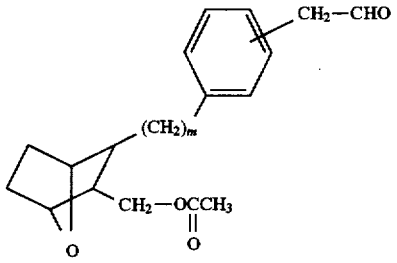

The above aldehyde is oxidized and esterified to the corresponding acetate ester, deprotected, and subjected to a Jones oxidation to form carboxylic acid II where n is 1.

U.S. Pat. No. 5,399,725 to Poss et al discloses a method for preparing an intermediate used in preparing compounds disclosed in U.S. Pat. No. 5,100,889 to Misra et al. In the Poss et al patent, an aldehyde

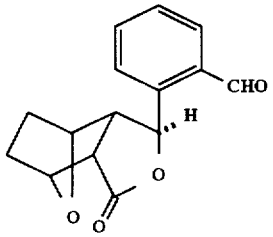

is prepared and subjected to a Horner-Emmons reaction to form the ester of the structure

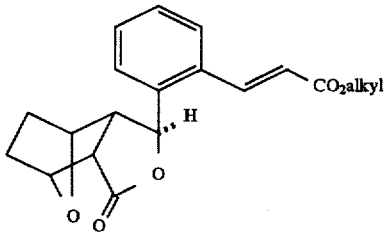

The ester is hydrogenated to the carboxylic acid II described with respect to the Misra et al U.S. Pat. 5,100,889, which may be used in making the final anti-thrombotic—anti-vasospastic compounds as disclosed in U.S. Pat. No. 5,100,889 to Misra et al.

DESCRIPTION OF THE INVENTION

In accordance with the present invention, methods are provided for preparing intermediates for use in the preparation of 7-oxabicycloheptyl substituted oxazole amide prostaglandin analogs as described hereinafter which are useful as anti-thrombotic and anti-vasospastic compounds.

The methods of the invention are outlined in Reaction Schemes I to III set out hereinafter.

Scheme I
Preparation of Acetal-type Intermediate IX
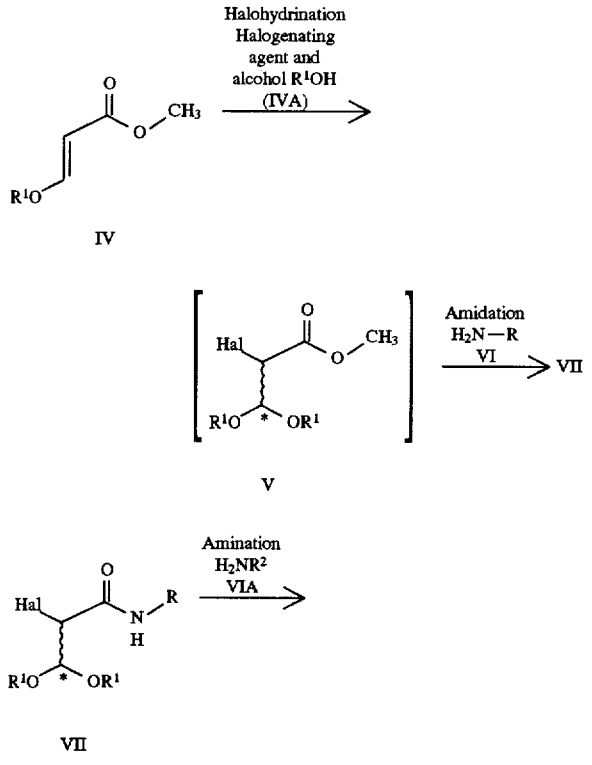
-continued
Scheme I
Preparation of Acetal-type Intermediate IX
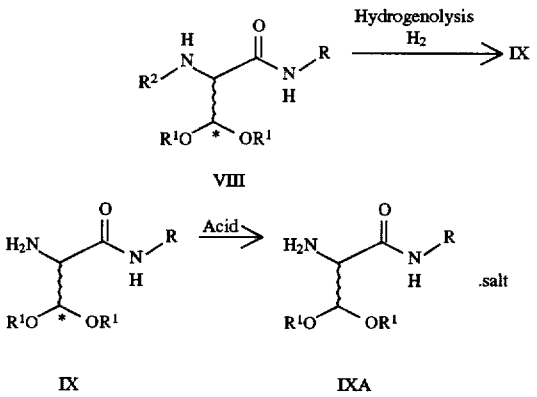
Scheme II
Preparation of 7-Oxabicycloheptane Intermediate XII
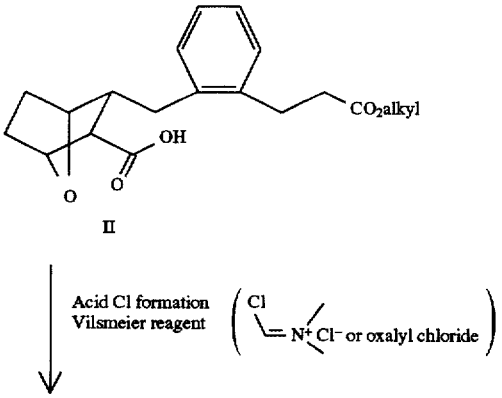

-continued

Scheme II

Preparation of 7-Oxabicycloheptane Intermediate XII

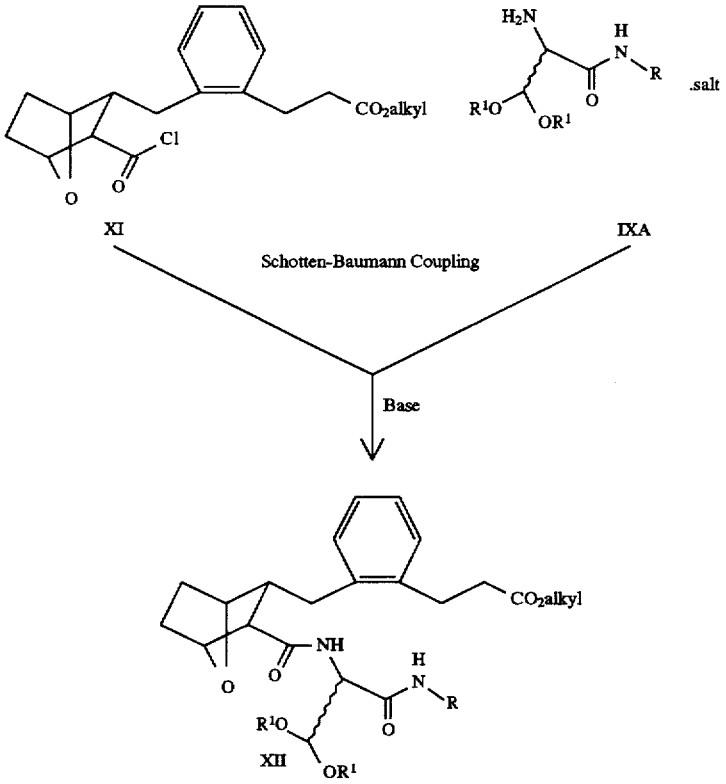

Scheme III

Preparation of Intermediate XIII and Final Product XIV

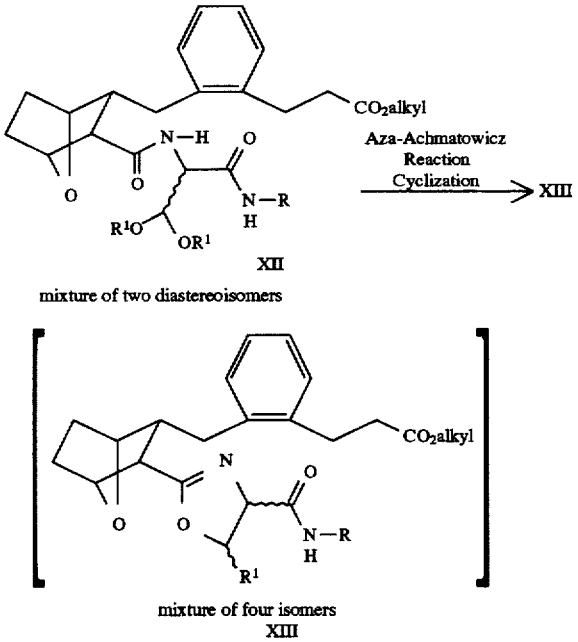

-continued

Scheme III

Preparation of Intermediate XIII and Final Product XIV

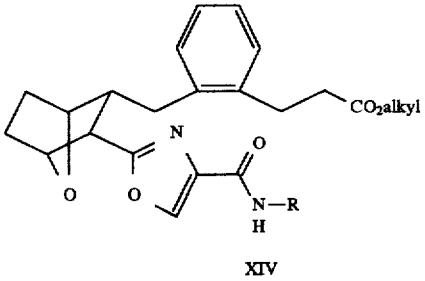

Referring to the above Reaction Schemes, as seen in Reaction Scheme I, one aspect of the present invention includes a method for preparing an amide intermediate of the structure IX

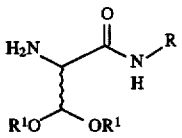

IX (which is a novel compound)

wherein R is alkyl, aryl, arylalkyl or cycloalkyl; and $R^1$ is alkyl, arylalkyl or cycloalkyl.

As shown in Scheme I, in accordance with the present invention, a method is provided for preparing intermediate amide IX from intermediate amide compound of the structure VIII

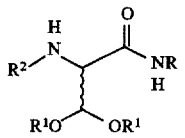

VIII (which is a novel compound)

wherein $R^2$ is aryl or arylalkyl, and $R^1$ and R are as defined above, by subjecting amide compound VIII to hydrogenolysis to form amide IX

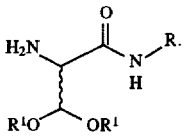

IX

The hydrogenolysis of VIII preferably is carried out by treating VIII with hydrogen in the presence of an alcohol, such as methanol.

In addition, as seen in Scheme I, in accordance with the present invention, the intermediate compound VIII is prepared by subjecting intermediate halo compound of the structure VII

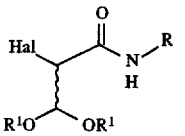

VII (which is a novel compound)

wherein R and $R^1$ are as defined above, to an amination reaction by reacting VII with an amine of the structure

VIA $R^2$—$NH_2$ wherein $R^2$ is as defined above.

In another aspect of the invention, as seen in Scheme I, intermediate halo compound VII

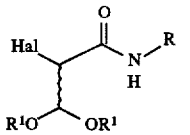

VII is prepared by subjecting a compound of the structure

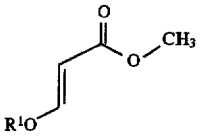

IV to a halohydrin reaction by reacting IV with a halogenating agent such as a halosuccinimide or dibromodimethylhydantoin (DBDMH), preferably N-bromosuccinimide, in the presence of an alcohol IVA (IVA) $R^1OH$ wherein $R^1$ is as defined above, such as methanol or ethanol, preferably methanol, to form compound V

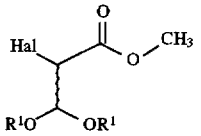

V (wherein $R^1$ is preferably alkyl)

and subjecting compound V to an amidation reaction by reacting V with an amine of the structure VI

VI $H_2N$—R (wherein R is as defined above) to form compound VII.

In yet another aspect of the present invention, referring to Reaction Scheme II, a method is provided for preparing intermediate compound of the structure XII

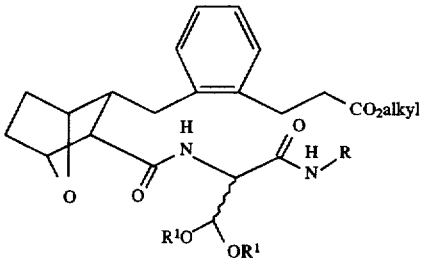

XII wherein R and $R^1$ are as defined above, which includes the steps of reacting starting acid II preferably with Vilsmeier reagent in the presence of an inert organic solvent such as toluene, to form acid chloride XI, subjecting acid chloride XI

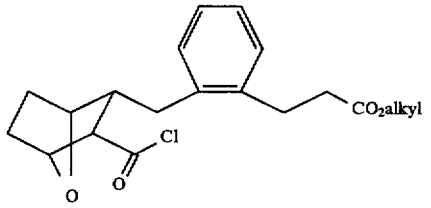

XI and compound IX of the structure

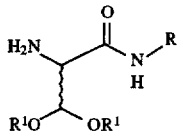

IX wherein R and $R^1$ are as defined above, to a coupling reaction, to form compound XII.

In a preferred embodiment of the invention, the coupling reaction is a Schotten-Baumann coupling carried out in the presence of a weak base, such as sodium bicarbonate.

Referring to Reaction Scheme III, in accordance with the present invention, a method is provided for forming a thromboxane receptor antagonist of the structure XIV

XIV

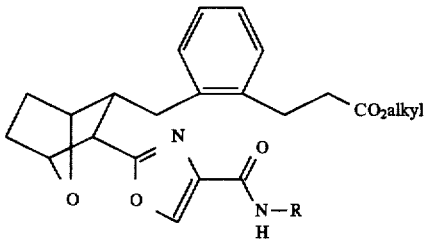

wherein R is as defined above, wherein compound XII is treated with a cyclizing agent, preferably trimethylsilyl trifluoromethane-sulfonate (TMSOTf) or chlorosulfonic acid, to form a mixture of four isomers XIII

XIII

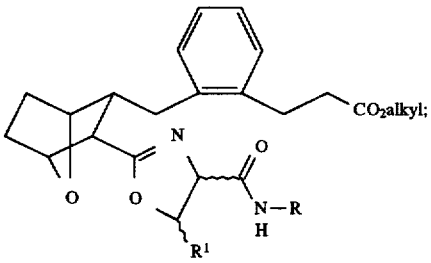

the mixture of isomers XIII is subject to an elimination reaction wherein XIII is treated with a base, preferably sodium methoxide or potassium t-butoxide/butanol, in the presence of an inert organic solvent, such as ethylene glycol dimethyl ether (also referred to as 1,2-dimethoxyethane or DME) or methyl acetate, to form thromboxane receptor antagonist XIV.

Alternatively product XIV may be prepared directly from XII by reacting XII with titanium tetrachloride/2,6-lutidine.

In addition, in accordance with the present invention, novel intermediates are provided having the following formulae:

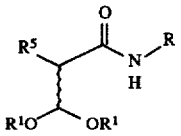

wherein R is alkyl, aryl, arylalkyl or cycloalkyl;

$R^1$ is alkyl, arylalkyl or cycloalkyl;

$R^5$ is amino, halogen (Halo), preferably Br, $R^2$—NH (where $R^2$ is aryl or arylalkyl), alkyl, aryl, arylalkyl or cycloalkyl.

Thus the novel intermediates of the invention include the following type compounds:

VII

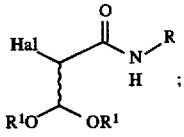

VIII

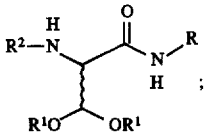

-continued

IX

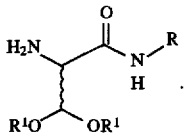

It is preferred that $R^1$ is alkyl such as methyl, $R^2$ is arylalkyl such as benzyl, and R is alkyl such as n-pentyl.

In addition, novel intermediates of the invention include compounds of the formula

XII

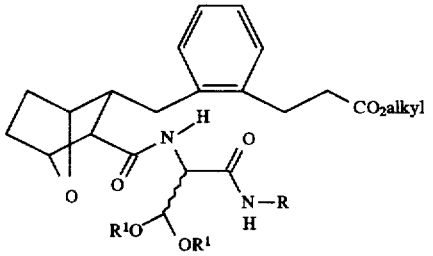

where R and $R^1$ are as defined above.

It is preferred that $R^1$ is alkyl such as methyl, alkyl is methyl, and R is alkyl such as n-pentyl.

DETAILED DESCRIPTION OF THE INVENTION

In carrying out the method of the invention as outlined in Reaction Scheme I for preparing intermediate IX, the acrylate starting material IV is subjected to a halohydrin reaction with a halogenating agent such as halosuccinimide, such as N-bromosuccinimide, N-chlorosuccinimide or N-iodosuccinimide or dibromodimethylhydantoin (DBDMH), preferably N-bromosuccinimide, and an alcohol $R^1OH$ (IVA), for example, methanol, ethanol, or isopropanol, preferably methanol, at a temperature within the range from about 15° to about 35° C., preferably from about 20° to about 30° C., (to form propanoic acid V) employing a molar ratio of halogenating agent:IV within the range from about 0.5:1 to about 2:1, preferably from about 0.75:1 to about 1.25:1.

The resulting propanoic acid V is amidated by reacting V with amine VI (to form halo compound VII) under an inert atmosphere such as argon or nitrogen, preferably nitrogen, at a temperature within the range of from about 15° to about 35° C., preferably from about 20° to about 30° C., employing a molar ratio of amine VI:V within the range from about 0.75:1 to about 4:1, preferably from about 1:1 to about 2:1.

Halo compound VII is subjected to an amination reaction with amine VIA (to form amide VIII) under an inert atmosphere such as argon or nitrogen, preferably nitrogen, at an elevated temperature within the range from about 80° to about 140° C., preferably from about 90° to about 120° C., employing a molar ratio of amine VIA:VII with the range from about 0.75:1 to about 5:1, preferably from about 1:1 to about 4:1.

The intermediate amide IX is then formed by hydrogenolysis of amide VIII wherein VIII is dissolved in an inert organic solvent, such as an alcohol such as methanol, ethanol or isopropanol, tetrahydrofuran (THF), or DME, preferably methanol, and the resulting solution is treated with hydrogen in the presence of a hydrogenolysis catalyst, preferably Perlman catalyst (20% $Pd(OH)_2$–50.8% $H_2O$), although other catalysts such as palladium on carbon, platinum on carbon, may be employed.

Amide IX is then converted to a salt IXA such as the corresponding oxalate, acetate or fumarate by treating a solution of amide IX in alcohol solvent such as methanol, ethanol or isopropanol, preferably methanol, with an acid such as oxalic acid, acetic acid or fumaric acid, preferably oxalic acid, at a temperature within the range from about 15° to about 35° C., preferably from about 20° to about 30° C., employing a molar ratio of acid:IX within the range from about 0.75:1 to about 3:1, preferably from about 1:1 to about 2:1, to form salt IXA, which is an intermediate for preparing thromboxane receptor antagonists.

Referring to Reaction Scheme II, the 7-oxabicycloheptane intermediate XII is prepared by subjecting acid II to acid chloride formation by treating acid II preferably with Vilsmeier reagent [(chloromethylene)dimethyl ammonium chloride], or other reagents such as oxalyl chloride, phosphorus pentachloride or thionyl chloride, in the presence of an inert organic solvent such as toluene, methylene chloride or diethyl ether, preferably toluene, under an inert atmosphere such as argon or nitrogen, preferably nitrogen, at a temperature within the range from about 15° to about 35° C., preferably from about 20° to about 30° C.

The resulting acid chloride XI is made to undergo a coupling reaction, preferably a Schotten-Baumann coupling, with amide IXA to form 7-oxabicycloheptane intermediate XII. In carrying out the Schotten-Baumann coupling reaction, acid chloride XI, in an inert organic solvent such as ethyl acetate, methyl acetate, methylene chloride or diethyl ether, preferably ethyl acetate, and coupling agent which is a weak base such as an alkali metal bicarbonate, for example sodium bicarbonate, potassium bicarbonate or lithium bicarbonate, preferably sodium bicarbonate, are reacted with amide IXA, at a temperature within the range from about −15° to about 20° C., preferably from about −10° to about 15° C., employing a molar ratio of IXA:XI within the range from about 0.75:1 to about 3:1, preferably from about 1:1 to about 2:1, and a molar ratio of coupling agent:XI within the range from about 2:1 to about 8:1 preferably from about 3:1 to about 6:1.

Intermediate XII may also be prepared employing other coupling reactions, for example, reacting acid chloride XI and amide IXA employing coupling reagents such as an organic base like piperidine, triethylamine, or diisopropylethylamine, at a temperature within the range from about −70° to about −55° C., preferably −78° C. Molar ratios of coupling agent:XI will be as described above in the Schotten-Baumann coupling.

The resulting 7-oxabicycloheptane intermediate XII is employed to form thromboxane $A_2$ receptor antagonist XIV.

Referring to Reaction Scheme III, thromboxane $A_2$ receptor antagonist XIV is prepared by subjecting compound XII to a cyclization reaction, preferably an Aza-Achmatowicz reaction wherein compound XII is dispersed in a reagent or solvent such as 1,2-dimethoxyethane (DME), methyl acetate or methylene chloride, preferably DME, under an inert atmosphere such as argon or nitrogen, preferably nitrogen, and is reacted with a cyclizing agent, such as trifluoromethanesulfonate (TMSOTf), or a halosulfonic acid like bromosulfonic acid, chlorosulfonic acid or fluorosulfonic acid, preferably TMSOTf or chlorosulfonic acid. Where TMSOTf is employed as the cyclizing agent, the reaction will be carried out at a temperature within the range from about 15° to about 50° C., preferably from about 20° to about 40° C. Where a halosulfonic acid is employed as the cyclizing agent, the reaction will be carried out at a reduced temperature within the range from about −10° to about 10° C., preferably from about 0° to about 10° C. The molar ratio of cyclizing agent:XII employed will be within the range from about 0.75:1 to about 4:1, preferably from about 1:1 to about 3:1.

A mixture of four isomers XIII is obtained which is made to undergo an elimination reaction wherein XIII is reacted with an organic base such as an alkali metal alkoxide, such as sodium methoxide, potassium t-butoxide/butanol, lithium t-butoxide, lithium methoxide, preferably sodium methoxide or potassium t-butoxide/butanol, in the presence of an inert organic solvent such as ethylene glycol dimethyl ether (DME), methyl acetate, methylene chloride, preferably DME, at a temperature within the range from about −20° to about 10° C., preferably from about −5° to about 5° C. to form XIV.

In carrying out the elimination reaction, the organic base will be employed in a molar ratio to XIII within the range from about 1:1 to about 7:1, preferably from about 2.1:1 to about 6:1.

The above cyclization-elimination reaction is effected in a one-pot procedure. Furthermore, in compound XII, the carbon bearing an acetal has the same oxidation state as the oxazole in product XIV.

The cyclization-elimination sequence may also be carried out directly from XII in a one pot procedure by reacting XII with titanium tetrachloride/2,6-lutidine in a 1:2 molar ratio, at a temperature within the range from about 15° to about 45° C., preferably from about 20° to about 40° C., in the presence of an inert organic solvent such as methylene chloride or dichloroether, preferably methylene chloride, employing a molar ratio of titanium tetrachloride:XII within the range from about 2:1 to about 6:1, preferably from about 3:1 to about 5:1.

The so-formed thromboxane $A_2$ receptor antagonist XIV may then be hydrolyzed to a corresponding salt employing conventional techniques such as treatment with an aqueous solution of an alkali metal base and then aqueous acid to form the corresponding acid which may be treated with sodium methoxide, sodium 2-ethyl-hexanoate or sodium ethoxide to form corresponding salt in the presence of acetone/methanol.

The term "lower alkyl" or "alkyl" as employed herein includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 substituents such as halo, alkenyl, alkynyl, aryl, alkyl-aryl, haloaryl, cycloalkyl, or alkylcycloalkyl.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, and/or alkoxy groups.

The term "aryl" or "Ar" as employed herein refers to monocyclic or bicyclic aromatic groups containing from 6 to 10 carbons in the ring portion, such as phenyl or naphthyl. Aryl (or Ar), phenyl or naphthyl may include substituted aryl, substituted phenyl or substituted naphthyl, which may include 1 or 2 substituents on either the phenyl or naphthyl such as lower alkyl, trifluoromethyl, halogen (Cl, Br, I or F), alkylsulfonyl, and/or arylsulfonyl.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to Cl, Br, F or I, with Cl preferred.

The final compounds XIV and esters and salts thereof prepared by the method of this invention are thromboxane receptor antagonists and as such are useful as inhibitors of thromboxane receptor mediated actions. The term "thromboxane receptor antagonist" includes compounds which are so-called thromboxane $A^2$ receptor antagonists, thromboxane $A^2$ antagonists, thromboxane $A^2$/prostaglandin endoperoxide antagonists, TP-receptor antagonists, or thromboxane antagonists.

The compounds prepared by the method of the invention are also thromboxane synthetase inhibitors and thus are useful as inhibitors of thromboxane production.

Examples of various utilities of the compounds prepared by the method of the invention are set out in U.S. Pat. No. 5,100,889.

The following Examples represent preferred embodiments of the present invention. Unless otherwise indicated, all temperatures are expressed in degrees Centigrade.

EXAMPLE 1

2-Bromo-3,3-dimethoxypropanoic Acid, Methyl Ester

With protection from direct light, N-bromo-succinimide (16.7 g, 1.1 equiv.) was slurried in MeOH (150 mL). The slurry was cooled to 0° to 5° C. and methyl-transmethoxyacrylate (10 g, 86.9 mmol) was added dropwise over about 15 min. The reaction mixture became homogeneous about halfway into addition. The reaction mixture was warmed to ambient temperature and stirred until the GC area % ratio of input to output was <0.5 as judged by an in-process GC method[1]. The reaction mixture was worked up after 16 hours.

[1] GC Method GC system HP: 5890 series II Gas Chromatograph Head pressure: 12 psi Column: Restek RTx1 (methyl silicone) megabore 30 m×530μ Temp.program: 2 min @100° C.; ramp at 10° C./min to 250° C.; hold @250° C. for 15 min Injector: 175° C. Detector: 300° C. Inj. Vol: 1 μL Sample prep.: 10 mg product in 1 mL MeOH The reaction mixture was concentrated at <40° C. under vacuum to ~40 mL. The concentrated reaction mixture was diluted with EtOAc (~140 mL). The solution was successively washed with 1N $NaHCO_3$ (3×50 mL) and 3% (w/v) aqueous NaCl solution and the rich organic layer was concentrated to afford title compound as a clear liquid (19.6 g, ~99M % as is).

EXAMPLE 2

2-Bromo-3,3-dimethoxy-N-pentylpropanamide

To neat Example 1 compound (11.0 g, 48.6 mmol) was added neat n-amyl amine (11.83 mL, 102.1 mmol, 2.1 equiv.) under nitrogen at 0° to 5° C. The reaction mixture was warmed to ambient temperature and stirred until the GC area % ratio of input to output was <0.5 by the in-process GC method described in Example 1. The reaction was worked up after ~16 hours.

The reaction mixture was diluted with tert-butylmethyl ether (MTBE) (~150 mL) and was extracted successively with 1M aqueous $NaH_2PO_4$ (3×50 mL, pH 5 buffer) and 3% (w/v) aqueous NaCl solution (30 mL).

The rich washed organic layer was concentrated to ~50 mL at <40° C. under vacuum (~25" of Hg) and heptane (~100 mL) was added. The remaining MTBE was exchanged for heptane under vacuum and more heptane was added to a final volume of ~150 mL (~14 mL/g input). The heptane solution was cooled from 35° C. to ambient temperature to initiate crystallization of the product. The crystal slurry was stirred at ambient temperature for several hours. The crystal slurry was filtered, washed with cold (~50° C.) heptane and dried under vacuum at ambient temperature to afford title compound as a white crystalline solid (10.5 g, ~78M % as is).

EXAMPLE 3

3,3-Dimethoxy-N-pentyl-2-[(phenylmethyl)amino]-propanamide

To neat Example 2 compound (4.0 g, 14.2 mmol) was added neat benzyl amine (4.65 mL, 42.6 mmol, 3 equiv.) under nitrogen and the reaction mixture was heated at 100° C. to 110° C. until the GC area % ratio of input to output was <0.5 by the in-process GC method described in Example 1. The reaction mixture was worked up after 16 hours.

The reaction mixture was diluted with MTBE (~80 mL) and was extracted successively with Dl water (3×40 mL), 1M aqueous $NaH_2PO4$ (40 mL, pH 5 buffer) and 3% (w/v) aqueous NaCl solution (40 mL).

The rich washed organic was concentrated to afford title compound as a clear oil (4.0 g, ~92M % as is).

EXAMPLE 4

2-Amino-3,3-dimethoxy-N-pentylpropanamide, oxalate (1:1)

A. Preparation of Methanolic Solution of 2-Amino-3,3-dimethoxy-N-pentylpropanamide Example 3 compound (37.5 g, 121.6 mmol) was dissolved in methanol (150 mL) and the solution was transferred into a Buchi hydrogenator. The apparatus was purged with nitrogen. About 5.3 g of Perlman catalyst [20% $Pd(OH)_2$–50.8% $H_2O$] were added and the apparatus was purged with hydrogen. The hydrogenolysis was conducted at 40° C. (jacket temperature) and at 25 psi pressure of hydrogen. The progress of the reaction was followed by the in-process GC method described in Example 1. The reaction was judged to be complete when the GC area % ratio of input to output was <0.1. The hydrogenolysis was stopped after four hours by purging the apparatus with nitrogen.

The reaction mixture was filtered to remove the catalyst. The catalyst was rinsed with MeOH (~2×20 mL). The methanolic solution containing title compound (theoretical yield ~26.5 g) was concentrated under vacuum at <40° C. to a volume of ~60 mL (range 2 to 2.5 mL solution per gram of theoretical output of title compound).

B. Preparation of 2-Amino-3,3-dimethoxy-N-pentylpropanamide, oxalate (1:1)

Solid oxalic acid•2 $H_2O$ (16.8 g, 133.7 mmol, 1.1 equiv.) was added to the Part A methanolic solution at ambient temperature and the agitation was continued to dissolve the acid. Ethyl acetate (~100 mL) and MTBE (~150 mL) were added and the solution was seeded to initiate crystallization of title compound (1:1 salt). Within 0.5 hour, the slurry became thick. Additional MTBE (~250 mL) was added at ambient temperature over ~2 hours.

The crystal slurry was stirred at ambient temperature for about 12 hours. The slurry was filtered, washed with MTBE (2×50 mL) and dried in vacuo at 30° C. to 35° C. to afford 33.1 g (88.2%) of title product having an HPLC determined H1 of 99.7.

EXAMPLE 5

[1S-(exo,exo)]-2-[[3-[[[2,2-Dimethoxy-1-[(pentylamino)carbonyl]ethyl]amino]carbonyl]-7-oxabicyclo-[2.2.1]hept-2-yl]methyl] benzenepropanoic acid, methyl ester A. [1S-(1α,2α,3α,4α)]-2-[(3-Carboxy-7-oxabicyclo[2.2.1]hept-2-yl)methyl]benzenepropanoic acid chloride The Vilsmeier reagent [(chloromethylene)-dimethyl ammonium chloride] (5.83 g, 45.55 mmol) was charged to an oven-dried, nitrogen inerted round bottom flask. [1S-(1α,2α,3α,4α)]-2-[(3-Carboxy-7-oxabicyclo-[2.2.1]hept-2-yl)methyl]benzenepropanoic acid (9.69 g, 30.44 mmol) was added along with dry toluene (70 mL, KF <0.05). The solution was agitated at room temperature until the HPLC area % ratio of BMS-191867-01 to the corresponding methyl ester was <2% (reaction time 1 hr) (note 1).

B. [1S-(exo,exo)]-2-[[3-[[[2,2-Dimethoxy-1-[(pentylamino)carbonyl]ethyl]amino]carbonyl]-7-oxabicyclo-[2.2.1]hept-2-yl]methyl]benzenepropanoic acid, methyl ester Crude Part A compound (7.95 g, 36.47 mmol as is) was diluted in 270 mL EtOAc and cooled to 0°–10° C. To this, 60 mL DI water and 145 mL of 1 N $NaHCO_3$ were added.

With vigorous agitation, the acid chloride solution was added to the biphasic Example 4 compound/$NaHCO_3$/EtOAc solution over 2.5 hr at 0°–10° C.

After addition, the reaction mixture was allowed to warm to ambient temperature.

The reaction mixture was heated to 45°–50° C. to achieve two clear phases. The lower spent aqueous phase was separated and the upper rich organic phase was washed with 1 N aqueous $NaHCO_3$ (60 mL) followed by DI water (2×60 mL). During work-up, the temperature was maintained at 45°–50° C. to prevent the product from crystallizing out.

The rich organic layer was cooled to 25° C. Product crystallization occurred before reaching 25° C. When the product slurry reached 25° C., 540 mL of n-heptane was added. The product cake was filtered and washed with 90 mL of n-heptane-EtOAc (75:25). The cake was dried in a vacuum oven at 40°–45° C. to afford 13.7 g (86.8 M % as is, Lab HI 98.6 for the combined diastereomers) of title compound as a white crystalline solid.

Notes

1) HPLC method:

Column: Novapak phenyl, 3.9×150 mm; Flow rate: 1 mL/min; Detection: 215 nm

Mobile phase: Solvent A: 75% $KH_2PO_4$ (0.02M, pH 4.5 with $H_3PO_4$)+25% $CH_3CN$ Solvent B: 40% DI water+60% $CH_3CN$ Gradient program:

| Time (min) | Solvent A | Solvent B |
|---|---|---|
| 0 | 100 | 0 |
| 10 | 100 | 0 |
| 40 | 0 | 100 (linear gradient) |
| 60 | 0 | 100 |

EXAMPLE 6

[1S-(1α,2α,3α,4α)]-2-[[3-[4-[(Pentylamino) carbonyl]-2-oxazolyl]-7-oxabicyclo[2.2.1]hept-2-yl] methyl]-benzenepropanoic acid, methyl ester Example 5 compound (20.72 g, 40 mmol) was slurried in 1,2-dimethoxyethane (280 mL) under $N_2$ and heated to 38° C. Trimethylsilyl trifluoromethane-sulfonate (TMSOTf) (11.5 mL, 60 mmol; 1.5 equiv.) was added. The solid quickly dissolved and the reaction was stirred until done by HPLC (used 2 additional charges of TMSOTf totalling 1.6 mL, 8 mmol), typically 2 h. A mixture of four oxazolines was obtained. The reaction mixture was cooled to −13° C. and a solution of 25 wt. % NaOME/MeOH (26.3 mL, 115 mmol) was added to it rapidly keeping the temperature below 1° C. The reaction was typically over after 1 h of the addition of the base. The slurry was quenched with 10% HCl (43 mL) and then water (25 mL) was added to dissolve the salts. The solution was warmed to 45° C. and treated with water (215 mL) to crystallize the product. The solid was collected by filtration and washed twice with 1:2 DME/water. Title compound was obtained as an off-white solid in 92% weight yield with a lab HPLC HI of 99.

EXAMPLE 7

[1S-(1α,2α,3α,4α)]-2-[[3-[4-[(Pentylamino) carbonyl]-2-oxazolyl]-7-oxabicyclo[2.2.1]hept-2-yl] methyl]-benzenepropanoic acid, methyl ester Example 5 compound (15 g, 28.92 mmol) was slurried in anhydrous methyl acetate under $N_2$ and cooled to 0C. Chlorosulfonic acid (4.04 ml, 60.78 mmol, 2.1 eq.) was added. The solid quickly dissolved and the reaction was stirred for 2 h. A mixture of four oxazolines was obtained. This colorless solution was added dropwise by cannulation over 55 min. to a 0° C. solution of 1M potassium t-butoxide/t-butanol (144.6 ml, 144.6 mmol, 5.0 eq.) and anhydrous methyl acetate (52.5 ml). The reaction was done by the end of the addition. The slurry was quenched with 1 M HCl until neutral (24 ml), and then water (150 ml) was added to dissolve the salts. The water layer was separated. The organic layer was washed again with water (2×150 ml). The combined aqueous washes were extracted once with methyl acetate (150 ml). This second extract was washed once with water (50 ml). The organic extracts were combined, concentrated, and exchanged into ethanol. 1/15th of this solution was removed for another experiment. The remaining volume was adjusted to 140 ml. The solution was warmed to reflux and treated with water (185 ml) until cloudy to crystallize the product. The solid was collected by filtration and washed twice with cold 20% ethanol/water. Title compound (11.55 g) was obtained as an off-white solid in 94.1% weight yield with 98.4% HI.

What is claimed is:

1. A method for preparing a compound of the structure

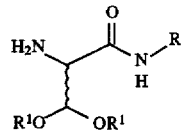

wherein R is alkyl, aryl, arylalkyl or cycloalkyl and $R^1$ is alkyl, arylalkyl or cycloalkyl, which comprises providing a compound of the structure

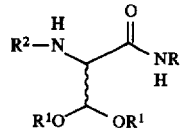

wherein $R^2$ is aryl or arylalkyl, and subjecting the above compound to hydrogenolysis to form a compound of the structure

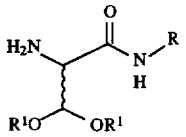

2. The method as defined in claim 1 wherein $R^1$ is $CH_3$ and R is n-pentyl.

3. The method as defined in claim 1 wherein the hydrogenolysis is carried out by treatent with hydrogen in the presence of hydrogenolysis catalyst.

4. The method as defined in claim 1 wherein the starting compound

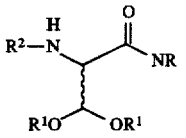

is prepared by subjecting a compound of the structure

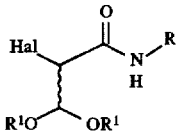

to an amination reaction by reacting with an amine of the structure $R^2—NH_2$.

5. The method as defined in claim 4 wherein $R^1$ is alkyl, $R^2$ is arylalkyl, R is alkyl, and Hal is Br.

6. The method as defined in claim 4 wherein the compound of the structure

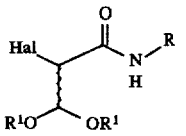

is prepared by subjecting a compound of the structure

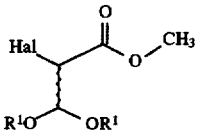

to an amidation reaction by reacting with an amine of the structure $H_2N—R$.

7. The method as defined in claim 6 wherein the compound of the structure

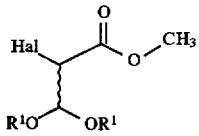

wherein $R^1$ is alkyl, is prepared by subjecting a compound of the structure

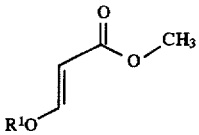

to a halohydrin reaction by reacting with a halogenating agent and an alcohol $R^1OH$.

8. The method as defined in claim 6 wherein the halohydrin reaction is carried out by reacting the compound of the structure

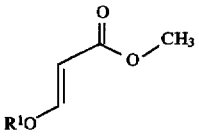

with N-bromosuccinimide and methanol, wherein $R^1$ is alkyl.

9. A method for preparing a compound of the structure

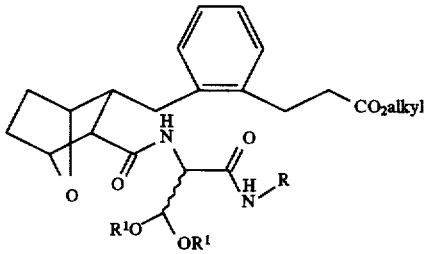

wherein R is alkyl, aryl, arylalkyl or cycloalkyl and $R^1$ is alkyl, arylalkyl or cycloalkyl; which comprises reacting an acid chloride of the structure

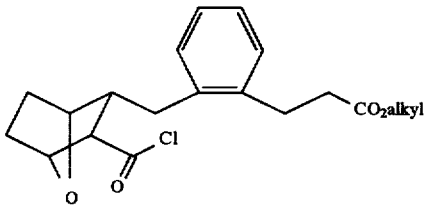

and a compound of the structure

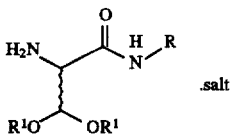

.salt wherein R is alkyl, aryl, arylalkyl of cycloalkyl and $R^1$ is alkyl, arylalkyl or cycloalkyl; in acoupling reaction to form a compound of the structure

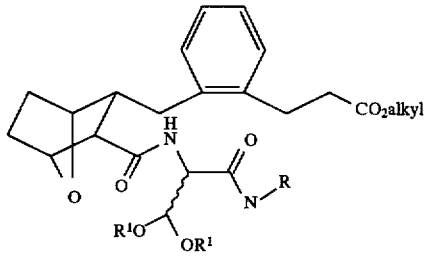

10. The method as defined in claim 9 wherein the coupling reaction is a Schotten-Baumann coupling carried out in the presence of a base at a temperature within the range from about −15° to about 20° C.

11. A method for preparing a compound of the structure

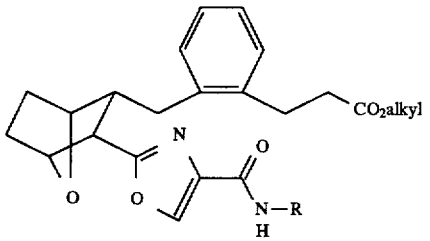

which comprises providing a starting compound of the structure

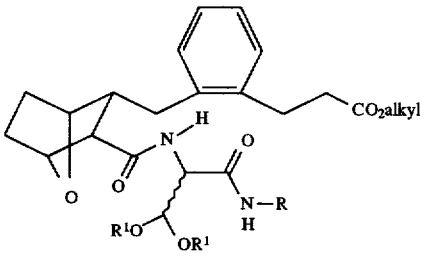

wherein R is alkyl, aryl, arylalkyl or cycloalkyl and $R^1$ is alkyl, aryl, arylalkyl or cycloalkyl, treating the above compound with a cyclizing agent to form a mixture of isomers of the structure

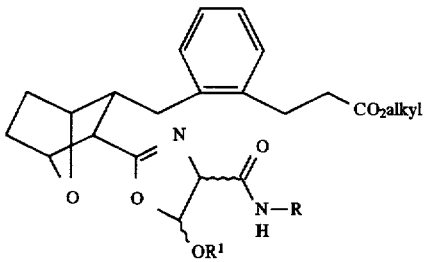

and subjecting the above isomers to an elimination reaction to form the thromboxane receptor antagonist.

12. The method as defined in claim 11 wherein cyclization is achieved by reacting the starting compound with trimethylsilyl trifluoromethane sulfonate.

13. The method as defined in claim 11 wherein the elimination reaction is achieved by reacting the mixture of isomers with an organic base which is an alkali metal alkoxide.

14. The method as defined in claim 12 wherein the cyclization is carried out at a temperature within the range from about 15° to about 50° C.

15. The method as defined in claim 11 wherein R is n-pentyl and alkyl is $CH_3$.

16. The method as defined in claim 11 wherein cyclization is achieved by reacting the starting material with a halosulfonic acid.

17. The method as defined in claim 16 wherein the halosulfonic acid is chlorosulfonic acid, bromosulfonic acid or fluorosulfonic acid.

18. The method as defined in claim 16 wherein the halosulfonic acid is chlorosulfonic acid.

19. The method as defined in claim 16 wherein the elimination reaction is achieved by reacting the mixture of isomers with potassium t-butoxide/butanol.

20. A compound having the structure

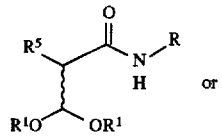

or

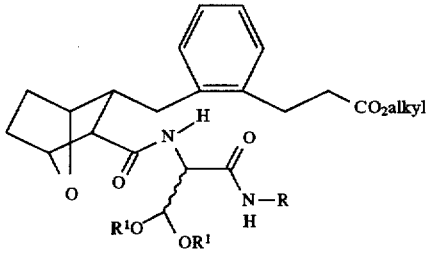

wherein R is alkyl, aryl, arylalkyl or cycloalkyl;

$R^1$ is alkyl, arylalkyl or cycloalkyl;

$R^2$ is aryl or arylalkyl;

$R^5$ is amino, halogen, $R^2NH$, alkyl, aryl, arylalkyl or cycloalkyl.

21. The compound as defined in claim 20 having the structure

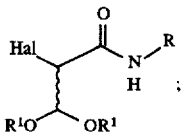

-continued
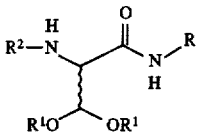
or
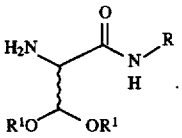
22. A compound as defined in claim 20 having the structure
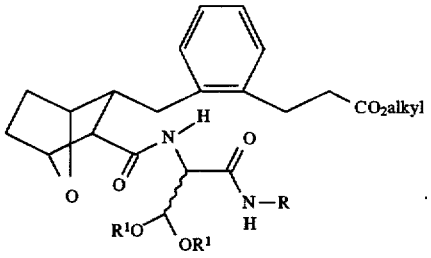
* * * * *